(12) United States Patent
Liljegren (10) Patent No.: US 10,441,289 B2
(45) Date of Patent: Oct. 15, 2019

(54) AIRWAY VALVE WITH ANCHORS

(71) Applicant: SPIRATION, INC., Redmond, WA (US)

(72) Inventor: Erik Liljegren, Redmond, WA (US)

(73) Assignee: SPIRATION, INC., Redmond, WA (US)

( * ) Notice: Subject to any disclaimer, the term of this patent is extended or adjusted under 35 U.S.C. 154(b) by 0 days.

(21) Appl. No.: 16/080,495

(22) PCT Filed: Jan. 31, 2017

(86) PCT No.: PCT/US2017/015711
§ 371 (c)(1),
(2) Date: Aug. 28, 2018

(87) PCT Pub. No.: WO2017/172021
PCT Pub. Date: Oct. 5, 2017

(65) Prior Publication Data
US 2019/0029691 A1    Jan. 31, 2019

Related U.S. Application Data

(60) Provisional application No. 62/315,075, filed on Mar. 30, 2016.

(51) Int. Cl.
*A61F 2/20* (2006.01)
*A61B 17/12* (2006.01)
(Continued)

(52) U.S. Cl.
CPC .. *A61B 17/12104* (2013.01); *A61B 17/12036* (2013.01); *A61B 17/12172* (2013.01);
(Continued)

(58) Field of Classification Search
CPC ............. A61F 2/20; A61F 2002/044; A61B 2017/242; A61B 2017/00541
(Continued)

(56) References Cited

U.S. PATENT DOCUMENTS 5,855,601 A     1/1999   Bessler
7,451,765 B2 *  11/2008  Adler ............... A61B 17/12104
                                                   128/200.26
(Continued)

FOREIGN PATENT DOCUMENTS

WO     2003079944        10/2003
WO     WO-03079944 A1 *  10/2003
(Continued)

OTHER PUBLICATIONS

International Search Report, PCT/US2017/015711 (WO2017/172021 A1) dated May 16, 2017.

*Primary Examiner* — Suzette J Gherbi
(74) *Attorney, Agent, or Firm* — The Dobrusin Law Firm, P.C.; Daniel P. Aleksynas (57) ABSTRACT

A valve (2) comprising: (a) membrane (50) and (b) a frame (10) in communication with the membrane so that the frame expands the membrane, the frame including: (i) a rod (4), (ii) a plurality of struts (12) connected to the rod at a distal end and extending generally radially outward as the struts extend away from the distal end and towards a proximal end; (iii) a plurality of anchors (30) that are in direct communication with the struts between the distal end and the proximal end, each of the plurality of anchors extending through an exit location (52) in the membrane.

20 Claims, 4 Drawing Sheets

(51) Int. Cl.
*A61F 2/24* (2006.01)
*A61F 2/04* (2013.01)

(52) U.S. Cl.
CPC .......... *A61B 17/12177* (2013.01); *A61F 2/24* (2013.01); *A61F 2002/043* (2013.01); *A61F 2220/0016* (2013.01); *A61F 2230/0093* (2013.01)

(58) Field of Classification Search
USPC .......................................................... 623/9
See application file for complete search history.

(56) References Cited

U.S. PATENT DOCUMENTS

| | | | |
|---|---|---|---|
| 7,670,373 B1* | 3/2010 | Sabanathan | A61B 17/12022 128/207.15 |
| 7,691,151 B2* | 4/2010 | Kutsko | A61B 17/12022 128/200.24 |
| 8,257,381 B2* | 9/2012 | Dillard | A61B 17/12104 128/207.14 |
| 8,603,127 B2* | 12/2013 | Alferness | A61B 17/12022 128/200.24 |
| 8,974,527 B2* | 3/2015 | Gonzalez | A61B 17/12022 623/9 |
| 9,622,752 B2* | 4/2017 | Gonzalez | A61B 17/12022 |
| 2003/0050648 A1* | 3/2003 | Alferness | A61B 17/12022 606/108 |
| 2003/0127090 A1* | 7/2003 | Gifford | A61M 16/0057 128/200.24 |
| 2003/0154988 A1* | 8/2003 | Devore | A61B 17/12022 128/207.15 |
| 2003/0158515 A1 | 8/2003 | Gonzalez et al. | |
| 2005/0033344 A1* | 2/2005 | Dillard | A61B 17/12104 606/191 |
| 2006/0102186 A1 | 5/2006 | Adler | |
| 2014/0031849 A1* | 1/2014 | Gonzalez | A61B 17/12022 606/191 |
| 2017/0035562 A1* | 2/2017 | Quadri | A61F 2/2418 |
| 2017/0281330 A1* | 10/2017 | Liljegren | A61F 2/04 |

FOREIGN PATENT DOCUMENTS

| | | |
|---|---|---|
| WO | 2004103209 | 12/2004 |
| WO | 2013040431 | 3/2013 |

* cited by examiner

AIRWAY VALVE WITH ANCHORS

FIELD

The present teachings generally relate to a valve that is compact and has a reduced length, the valve also includes anchors that are extend from the struts so that the valve does not settle once deployed.

BACKGROUND

Mechanical airway valves are placed within a passageway to prevent air from flowing in selected portions of a lung.

It would be attractive to have a valve with anchors and struts located within the same region. What is needed is a valve that expandable to both anchor to a passageway and seal a passageway so that pre-measuring a length and/or cross-sectional length is not required. It would be attractive to have a valve with anchors extending directly from the struts. What is needed is a valve with anchors that are free of settling so that the valve substantially retains its position once deployed.

SUMMARY

The present teachings meet one or more (if not all) of the present needs by providing a valve comprising: (a) membrane and (b) a frame in communication with the membrane so that the frame expands the membrane, the frame including: (i) a rod, (ii) a plurality of struts connected to the rod at a distal end and extending generally radially outward as the struts extend away from the distal end and towards a proximal end; (iii) a plurality of anchors that are in direct communication with the struts between the distal end and the proximal end, each of the plurality of anchors extending through an exit location in the membrane.

The teachings herein surprisingly solve one or more of these problems by providing a valve with anchors and struts located within the same region. The present teachings provide a valve that expandable to both anchor to a passageway and seal a passageway so that pre-measuring a length and/or cross-sectional length is not required. The present teachings provide a valve with anchors extending directly from the struts. The present teachings provide a valve with anchors that are free of settling so that the valve substantially retains its position once deployed.

DETAILED DESCRIPTION

The explanations and illustrations presented herein are intended to acquaint others skilled in the art with the invention, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings provide an improved valve for placement in a passageway. The present teachings provide an improved airway valve. The valve functions to gradually open in an airway and block airflow through that airway. The valve may seal one or more structures such as passageways and preferably airways in a lung. Preferably, the valve forms a seal and prevents airflow in a bronchi, a bronchiole, a branch of a bronchi, a branch of a bronchiole, or a combination thereof. The valve may function to be removable. The valve may function to be biocompatible. The valve may extend along an axis. The valve may curve. The valve may be linear. The valve may bend in one or more locations, one or more directions, or both. The valve may bend and be rotatable. The valve may include one section. The valve may include a plurality of sections. The valve includes a distal end and a proximal end. The valve includes a longitudinal axis that extends from the distal end to the proximal end. The longitudinal axis may follow the shape of the valve such that the longitudinal axis is linear, arcuate, includes bends, or a combination thereof. Preferably, the longitudinal axis is a largest dimension of the valve and extends parallel to a length of the valve.

The distal end may be the lead end and/or first end placed into an airway. The distal end may include a fixed anchor. The distal end may include a terminal point, be a terminal end, or both. The distal end may include one or more blunt features so that during deployment, the distal end contacts a wall of the airway and moves the airway while the airway remains intact. If more than one valve section is present then each valve section may include a distal end. The distal end may be located opposite the proximal end. One or more of the distal ends of a valve section may be in communication with a proximal end of an adjacent valve section.

The proximal end may be the last end to be deployed. The proximal end may include one or more retraction features. The proximal end may include one or more removal features. The proximal end may include a rod.

The rod may function as a support, a support for the frame, a central axis, or a combination thereof. The one or more rods may extend along a longitudinal axis of the valve, may be the longitudinal axis of the valve, or both. The rod may be used to remove the valve from a structure. The rod may release the connection with the walls of the passage and/or airway. The rod may move the struts so that the struts are relaxed from the deployed state and the valve can be moved and/or removed. The distal end, the proximal end, or both may include one or more connection features, one or more removal features, one or more detachable features, or a combination thereof. The proximal end may include a bulbous portion, a hook, a hole, a "J" shape, or a combination thereof that assists in forming a connection so that the valve may be removed. The one or more rods may include one or more curves, one or more bends, or both. Preferably, the one or more rods may be generally straight (i.e., linear).

The one or more rods may be hollow, solid, or both. The one or more rods may be flexible. The one or more rods may be made of nitinol, steel, surgical steel, stainless steel, plastic, a polymer, a thermoset, a thermoplastic, or a combination thereof. The one or more rods may be movable in one direction to assist in centering the valve within a passageway and especially a structure. The one or more rods may include through holes, dimples, indentations, recesses, raised sections, non-linear sections, or a combination thereof. The one or more rods may each include a distal end and a proximal end. The valve may include a plurality of rods that are connected together by one or more hinge points so that the valve may move through a non-linear path (e.g., a tortuous path).

The proximal ends may include one or more hinge points, one or more interconnects, or both. The valve may include more than one proximal end when the valve includes more than one valve section. The valve may include two or more sections and even a plurality of sections.

The one or more sections may function to individually seal an airway or anchor to an airway. The one or more sections may function to seal a length of a passage, an airway, or both. Each of the one or more sections may be movable relative to one another. The one or more sections may be located along an axis. The one or more sections may be located end to end. The one or more sections may be located at an angle relative to each other (i.e., in a non-straight line). The one or more sections may connect to and/or block a passage or an airway. The one or more sections may be substantially identical. The one or more sections may be movable along a rod, fixed to a rod, or both. Two or more sections may be connected to a single rod (i.e., one unitary piece). Each section may be connected to its own rod. Preferably, the valve includes only one valve section. Each section may have a cross-sectional length (e.g., diameter (i.e., a distance radially outward from the rod)) in the fully deployed state of about 5 mm or more, about 6 mm or more, about 7 mm or more, about 8 mm or more, or even about 9 mm or more. The sections may have a cross-sectional length in the fully deployed state of about 20 mm or less, preferably about 15 mm or less, or more preferably about 12 mm or less. The sections may each have multiple cross sectional lengths. Preferably, the valve sections include multiple cross-sectional lengths. More preferably, each group of struts include a cross-sectional length and the cross-sectional lengths are different.

The valve section may include a frame that is covered by a membrane. The frame may function to move the membrane into contact with a passageway. The frame may function to secure the valve within a passageway. The frame may expand and contract. The frame may be the skeleton for the valve. The frame may provide longitudinal support for a membrane, radial support for the membrane, longitudinal support for the valve, or a combination thereof. The frame may be connected to a rod. The frame may move relative to the rod (e.g., expand radially away from the rod or move longitudinally relative to the rod). The frame may include one or more base members, one or more struts, one or more anchor connections, one or more anchors, or a combination thereof.

The base member may connect the struts, the anchors, or both to a rod. The base member and the struts, anchors, or both may be one integral piece. Each of the base members may function to axially move along a rod. The base members may function to axially restrict one end of a strut. The struts may be fixedly connected to the base member (e.g., welded, adhesively bonded, or both). The base member may be indirectly connected to the anchors by the struts. Each set of struts may include a base member. Two or more sets of struts may be connected to a single base member. The base member may lock to a rod. The base member may move along a rod. The base member may be movable to allow the struts to expand radially outward. Some base members may be axially movable, radially movable, or both and some base members may be static or immovable. The base member may be welded to the rod, have a hole and pin configuration, crimped on the rod, adhered, soldered, The base members may be generally toroidally shaped, doughnut shaped, or both. The base members may be cylindrical. The base member may include a through hole that a rod extends through, and a set of struts may extend radially outward from the base member.

Each set of struts may function to work together to seal all or a portion of an airway (seal as discussed herein means prevent air from passing beyond the valve). Each set of struts may include two or more struts, three or more struts, four or more struts, preferably five or more struts, or even six or more struts. The struts may be evenly distributed about the rod, the base member, or both. The struts may be asymmetrically distributed about the rod, the base member, or both. One set of struts may be aligned with another set of struts. One set of struts may be offset relative to another set of struts. For example, a first set of struts may include struts that are located in-between a second set of struts. One or more sets of struts may include a membrane. One set of struts may be free of a membrane. One set of struts may support the membrane when a first set of struts is compressed to a point where the membrane includes wrinkles or is not in contact with a passageway to seal a passageway. Both set of struts may include a membrane. One set of struts may be located fully and/or partially inside of another set of struts. One set of struts may extend longitudinally forward beyond a second set of struts. One set of struts may extend radially outward further than a second set of struts (i.e., extend further outward from a rod). For example, one set of struts (e.g., internal struts) may be located at least partially internal to a second set of struts (e.g., an external set of struts).

The one or more struts and preferably a plurality of struts may function to expand the membrane (i.e., struts). The one or more struts may function to move the membrane into contact with a structure (i.e., a passageway or an airway). Preferably, the one or more struts may function to move the membrane radially outward. The struts may be movable so that a force applied by the struts may be increased or decreased at a predetermined location. Each set of struts may exert a sufficient force on a passage or airway to form a seal with the passage or airway. Each set of struts may exert a sufficient force so that a passage and/or airway is blocked by a membrane in communication with the struts. Each strut may exert an outward force of about 0.01 Kg or more, about 0.04 Kg or more, about 0.06 Kg or more, or even about 0.08 Kg or more. Each strut may exert a force of about 1 Kg or less, about 0.5 Kg or less, about 0.25 or less, or even about 0.1 Kg or less. The struts may function to expand so that the struts and membrane seal an airway, a passageway, or both. The struts may function to elastically deform from a closed position (i.e., a retracted state) to an open position (i.e., deployed state). The struts may extend from being located along the longitudinal axis to extending radially outward. The one or struts may be formed into an open position and then closed until deployed where the struts elastically deform into the open position. Each strut may extend generally radially outward from a base member, a rod, or both. The struts may extend radially outward from the rod a distance of about 1 mm or more, about 2 mm or more, or about 3 mm or more. The struts may extend radially outward from the rod a distance of about 8 mm or less, about 6 mm or less, or about 4 mm or less. One set of struts may extend radially outward a larger distance than a second set of struts (e.g., one set of struts may extend outward a distance of about 1 mm or more, about 1.5 mm or more, about 3 mm or less than a second set of struts). When more than one set of struts are present a second set of struts may extend radially outward less than a first set of struts. A second set of struts may extend radially outward from the rod a distance that is about 90 percent or less, about 80 percent or less, about 75 percent or less, or about 60 percent or less than the first set of struts. A second set of struts may extend radially outward from the rod a distance that is about 30 percent or more, about 40 percent or more, about 45 percent or more, or about 50 percent or more than the first set of struts. Each strut may form a "J" shape. Each strut may include one or more bends, two or more bends, or even three or more bends. Each strut may curve so that the strut extends radially outward from the base member. The strut as it extends outward from the base member may curve so that the angle relative to the base member extends away from the rod, the base member, or both and then parallel to the rod. Each strut in a fully relaxed state may have at least a section that is parallel with a base member, a rod, or both. The struts have a length. Each of the struts may have an identical length. The length of the struts from valve section to valve section, from strut set to strut set, or both may vary or be the same. For example, the valve sections (or set of struts) at the distal end may have shorter struts then the valve sections at the proximal end so that the distal end may fit within or seal smaller passages and/or airways. Each strut may have a length of about 3 mm or more, about 4 mm or more, or even about 5 mm or more. Each strut may have a total length of about 10 mm or less, about 9 mm or less, or about 8 mm or less. The length of a first set of struts to a second set of struts may be about 90 percent or less, about 80 percent or less, about 75 percent or less, or about 60 percent or less than the second set of struts or vice versa. The length of a first set of struts to a second set of struts may be about 30 percent or more, about 40 percent or more, about 45 percent or more, or about 50 percent or more than the second set of struts or vice versa. Each strut may include one or more features for gripping tissue, a wall of a passage, a wall of an airway, or a combination thereof. Each strut may have a tip that curves inward, that extends towards the rod, or both. Preferably, the struts do not include a feature that penetrates a passage. The features that grip the passage may only do so by exerting a radially outward force. The struts may be made of any elastically deformable material. The struts may be made of a biocompatible material. The struts may be made of metal, plastic, polymeric material, an alloy, or a combination thereof. Preferably, the struts may be made of nitinol (i.e., a nickel titanium alloy). Some struts may be directly connected to a rod and some struts may be connected to a base member and the struts may be connected to a membrane that extends between the struts and along the struts from the tip to the rod. The one or more struts and a plurality of struts may be directly connected to an anchor by an anchor connector.

The one or more anchor connectors may function to connect an anchor directly to a strut. One anchor connector may function to connect one anchor to one strut. However, one strut may include an anchor connector an each side of a strut and two anchors may be connected to a single strut. One anchor may extend distally from an anchor connector and a second anchor may extend proximally from the same anchor connector. The valve may include 1 or more, 2 or more, or 3 or more anchor connectors. The valve may include 10 or less, 8 or less, or 6 or less anchor connectors. The anchor connector may be an integral part of the anchor, the strut, or both. The anchor connector, strut, and anchor may be made of the same single piece of material. The anchor connector may be connected to the strut, the anchor, or both. The anchor connector may be joined to the strut, the anchor or both by welding, soldering, friction welding, bonding, an adhesive, or a combination thereof. Every strut may include an anchor connector (i.e., every strut may include an anchor). Some of the struts may include anchors and anchor connectors. Every other strut may include an anchor connector. The anchor connector may extend laterally from the strut (i.e., in a direction substantially perpendicular to the longitudinal axis). The anchor connector may be an extension from a side of the strut, the anchor, or both. The anchor connector may be planar with the anchor, the strut, or both. The anchor connector may be offset relative to the strut, the anchor, or both. The anchor connector may overlap with the anchor, the strut, or both. The anchor connector may be folded relative to the anchor, the strut, or both (e.g., include a curved section that extends from and connects to the anchor, the strut, or both). The anchor connector may extend at an angle relative to the strut, the anchor, or both (i.e., towards the distal end or towards the proximal end). The anchor connector may extend at an angle of about 90 from the strut, the anchor, or both (i.e., relative to the longitudinal axis). The anchor connector may extend at an angle of about 1 degree or more, about 2 degrees or more, about 5 degrees or more, or even about 10 degrees or more in the proximal direction or the distal direction from a direction perpendicular to the longitudinal axis. Thus, for example, if the angle is about 1 degree in the distal direction then the anchor connector extends at an 89 degree angle from the strut towards the distal direction. The anchor connector may be flexible, rigid, include flexible regions, include breaks, include regions designed to flex, or a combination thereof. The material characteristics of the anchor connector may be such that the anchor connector is flexible. The anchor connector may be made of the same material as the anchor, the struts, or both. Preferably, the anchor connector is made of nitinol. The anchor connector may be substantially rigid. The anchor connector may be free of any flexible sections. The anchor connector may be free of rotation along the longitudinal axis. The anchor connectors may have a length, width, or both of about 0.5 mm or more, about 1 mm or more, or about 2 mm or more. The anchor connectors may have a length, width, or both of about 10 mm or less, about 7 mm or less, about 5 mm or less, or about 3 mm or less. The anchor connectors may connect to the struts on a first edge and then the anchors on a second edge that is 90 degrees from the first edge.

The one or more anchors may function to prevent movement of the valve when the valve is in the deployed state. The one or more anchors may function to prevent movement of one or more valve sections, one or more rods, the entire valve, or a combination thereof. The one or more anchors may function to prevent movement of the valve within a passage, an airway, or both so that the valve remains at a desired location. The one or more anchors may prevent axial movement of a valve section relative to a rod. The one or more anchors may be located at the distal end, the proximal end, or both ends of the valve. Preferably, the anchors extend from a central region of the valve (i.e., a location between the distal end and the proximal end). More preferably, the anchors extend from substantially the middle of the valve (i.e., within about 20 percent or less, about 15 percent or less, or about 10 percent or less of center). Each of the one or more anchors may extend in an opposing direction to the struts. The one or more anchors may extend away from a seal area of the valve. A distance may be located between the seal area of the valve and the anchors. The anchors and the seal area may be separated by a distance so that the valve cannot rotate relative to the passageway when deployed. The distance between the seal area an anchors (e.g., a part of the anchor that contacts a wall of a passage) may be about 1 mm or more, about 2 mm or more, about 3 mm or more, or even about 4 mm or more. The distance between the seal area and an anchor may be about 10 mm or less, about 9 mm or less, about 8 mm or less, about 7 mm or less, about 6 mm or less, or even about 5 mm or less. The anchors during deployment may extend substantially radially outward such that the distance from the anchors and the seal area is substantially the same in the deployed state, the retracted state, and a state therebetween. The anchors may deploy substantially radially outwards (e.g., may move an axial distance of about 2 mm or less, about 1 mm or less, about 0.5 mm or less). The anchors may move substantially radially outward so that during movement of the anchors the anchors are free of axially moving the valve (i.e., longitudinal movement within a passageway). The one or more anchors may include one or more arms that attach the valve to a structure, prevent movement of the valve, or both.

The one or more arms may function to connect the valve to a structure. The one or more arms may function to prevent movement of the valve when the valve is deployed. The one or more arms may extend radially outward from a rod. The one or more arms may be made of nitinol, steel, surgical steel, stainless steel, plastic, a polymer, a thermoset, a thermoplastic, or a combination thereof. The one or more arms may be comprised of one or more sections and preferably a plurality of sections or regions. The one or more arms may include first arcuate region, a second arcuate region, a third arcuate region, and an anchor tip.

The one or more anchor tips may function to grip a structure, anchor a structure, or both. The one or more anchor tips may function to prevent the arms of the anchor form moving relative to a structure. The one or more anchor tips may extend into contact with a structure, a passageway, tissue, or a combination thereof. The one or more anchor tips may have a tip that is pointed, blunt, rounded, flat, at an angle relative to the arms, or a combination thereof. The one or more anchor tips may extend outward beyond the main portion of the arms. The one or more anchor tips may be angled towards a distal end, a proximal end, or both. The anchor tips may extend at an angle of about 45 degrees or more, about 60 degrees or more, 75 degrees or more, or about 90 degrees or more from the second arcuate region, the arm to which the anchor tip is connected, or both. The anchor tip may extend at an angle of about 90 degrees from an anchor pad and the anchor pad may contact the passageway so that contact between the anchor tip and the tissue of the passageway is restricted. The anchor tips may extend at an angle of about 150 degrees or less, about 135 degrees or less, about 115 degrees or less, or about 105 degrees or less relative to the second arcuate region, the arm to which the anchor tip is connected, or both. Some anchor tips may extend at an angle relative to the arms, and some anchor tips may extend coplanar with the arms. The anchor tips may have a length of about 1 mm or more, about 2 mm or more, or about 3 mm or more. The anchor tips may have a length of about 10 mm or less, about 8 mm or less, or about 5 mm or less. The one or more anchor tips and arms may extend outward from the second arcuate region of the arm.

The second arcuate region may function to align the anchor tips towards the passageway. The second arcuate region may function orient the anchor tips so that the anchor tips grip tissue and prevent movement of the valve. The second arcuate portion may extend towards the distal end. The second arcuate region may extends radially outward from the rod, the longitudinal axis, or both. Preferably, the second arcuate region extends both distally and radially outward from the rod, the longitudinal axis, or both. The second arcuate region may extend towards the distal end by having one or more curves, arcs, arcuate segments, bends, or a combination thereof that form an angle of about 10 degrees or more, about 15 degrees or more, about 20 degrees or more, or even about 25 degrees or more. The second arcuate region may extend towards the distal end by having one or more curves, arcs, arcuate segments, or a combination thereof that form an angle of about 125 degrees or less, about 105 degrees or less, about 90 degrees or less, about 75 degrees or less, about 60 degrees or less, or about 45 degrees or less. The second arcuate region may have a segment that connects to the first arcuate region and a segment that connects to the anchor tip and those segments may form the angle discussed herein relative to each other. The second arcuate region may have a segment (e.g., a radial segment) that extends generally outward relative to the rod, the longitudinal axis, or both, and a segment (e.g., a longitudinal segment) that extends towards the distal end or the proximal end. The second arcuate region may have a segment that extends from a first direction towards a second region. The second arcuate region may provide a force radially outward so that the anchor tip grips tissue. The second arcuate region may prevent valve settling (i.e., movement of the valve after the valve has been set into a passageway). The second arcuate region may align the valve within the passageway so that the valve is immobilized and does not move during air moving into and/or out of the passageway. The second arcuate region may assist in anchoring the anchor tip so that the valve is immobilized. The second arcuate region may connect to and extend from a first arcuate region. The segment of the second arcuate segment that connects to the anchor tip may be substantially parallel (i.e., within ±5 degrees or less) of an attachment segment of the first arcuate region.

The first arcuate region may function to connect the anchor to the anchor connections, the struts, or both. The first arcuate region may function to form a connection and extend radially outward from the valve. The first arcuate region may extend towards the distal end, the proximal end, or both. The first arcuate region may connect to the anchor connection and extend substantially parallel (i.e., within ±5 degrees or less) with the longitudinal axis and then curve outward away from the rod, the longitudinal axis, or both. The first arcuate region may have a segment (i.e., a connection segment) that connects to the anchor connection and a segment (i.e., transition segment) that connects to the second arcuate region. The connection segment and the transition segment may be connected by one or more curves, arcs, arcuate segments, bends, or a combination thereof. The connection segment and the transition segment may form an angle. The angle between the connection segment and the transition segment may be about 15 degrees or more, about 25 degrees or more, about 45 degrees or more, or about 60 degrees or more. The angle between the connection segment and the transition segment may be about 180 degrees or less, about 160 degrees or less, about 135 degrees or less, or about 105 degrees or less. The first arcuate region may extend outward such that once the valve is placed the first arcuate region prevents settling, movement, or both. The first arcuate region may be at a resting state when the valve is fully deployed. The first arcuate region is angled so that the anchors move radially outward with substantially no axial movement (i.e., substantially free of axial movement (e.g., 1 mm or less)). The first arcuate region may extend through the membrane, an exit location of the membrane, or both.

The exit location may function to allow an anchor to pass from a first side of the membrane to a second side of the membrane. The exit location may permit the anchor to pass through the membrane without allowing air to pass through the membrane. The exit location may function to allow movement of the anchor without causing wrinkling of the membrane, damage to the membrane, air permeability, or a combination thereof. The exit location of the membrane may be formed around the anchor so that a substantially air tight seal is formed around each of the plurality of anchors. The exit location may be an absence of material. The exit location may be a through hole, a slit, a cut, or a combination thereof. The exit location may be elastically deformable so that the exit location maintains a seal around the anchor. The exit location may be an integral part of the membrane.

The membrane may function to prevent passage of fluids. The membrane may function to restrict airflow through a structure, a passageway, and preferably an airway. The membrane may be fluid impermeable. The membrane may be rigid. The membrane may be flexible. The membrane may be plastically deformable. Preferably, the membrane is elastically deformable. The membrane may be attached along a length of each strut. The membrane may be attached at one or more points on each strut. The membrane may substantially surround all or a portion of a strut (i.e., from the rod to the tip of each strut). The membrane may be in communication with one set of struts. The membrane may be located on one set of struts and contacted by a second set of struts if the membrane is restricted so that the struts are not fully deployed (i.e., deployed to about 95 percent or less, about 90 percent or less, about 85 percent or less, or about 80 percent or less than full deployment). The membrane may be made of a polyurethane, an aliphatic polycarbonate-based thermoplastic polyurethane, a polyethylene siloxane, a material that includes silicone, a silicone polyurethane, a fluoroelastomer, an acrylate polymer, a polyacrylate, or a combination thereof. The membrane may be made of a material with a modulus of elasticity of about 10 GPa or less, about 5 GPa or less, about 2 GPa or less, or even about 1 GPa or less. The material may have a modulus of elasticity of about 0.001 GPa or more, about 0.003 GPa or more, about 0.005 GPa or more, about 0.01 GPa or more, about 0.03 GPa or more, about 0.05 GPa or more, or even about 0.06 GPa or more. The material of the membrane may have a modulus of elasticity of from about 0.00100 GPA to about 0.065 GPa. A material with a tensile stress at 100 percent strain of about 3 MPa or more, about 5 MPa or more, or more preferably about 8 MPa or more, about 12 MPa or more, about 15 MPa or more, or even about 20 MPa or more. The material may have a tensile stress at 100 percent strain of about 100 MPa or less, about 50 MPa or less, or about 30 MPa or less. A material with a tensile stress at 200 percent strain of about 4 MPa or more, about 7 MPa or more, about 10 MPa or more, about 15 MPa or more, or about 20 MPa or more. The material may have a tensile stress at 200 percent strain of about 100 MPa or less, about 50 MPa or less, or about 30 MPa or less. A material with a tensile stress at 300 percent strain of about 6 MPa or more, about 9 MPa or more, about 13 MPa or more, about 18 MPa or more, or about 20 MPa or more. The material may have a tensile stress at 300 percent strain of about 100 MPa or less, about 50 MPa or less, or about 30 MPa or less. A material with a tensile strength at break of about 15 MPa or more, about 20 MPa or more, or about 25 MPa or more (i.e., between about 15 MPa and about 30 MPa). The material may have a tear strength of about 40 kN/m or more, about 60 kN/m or more, about 75 kN/m or more, about 100 kN/m or more. The material may have a tear strength of about 200 kN/m or less, about 150 kN/m or less, or about 125 kN/m or less. When more than one membrane is used, one membrane may be elastic and one membrane may be non-flexible. For example, one membrane may be made of a thermoplastic polyurethane and one membrane may be made of a silicone polyurethane. The membrane may stretch without wrinkling. The membrane may be stretched by a force of the struts expanding from a retracted state to a deployed state. The membrane may be connected to a set of struts, a base member or both. The two or more struts and preferably a plurality of struts may be connected to a base member.

The deployed state may function to seal a passage, an airway, or both. The deployed state may function to extend the struts radially outward to support a valve substantially within a center of a passage and/or an airway. The deployed state may have the struts fully deployed and the movable anchors moved to a steady state (i.e., fully deployed location) where further movement of the valve does not occur. The deployed state may have the struts extending radially outward. The fully deployed state may have the struts extending outward from the rod and into contact with a structure such as a passageway. The struts may be restricted from fully opening due to the structure such that a steady state is not achieved. The struts may gradually extend from the retracted state to the fully deployed state and may extend at an angle less than 90 degrees. The valve may slowly transition from a retracted state to a fully deployed state over time as the struts elastically deform back to a steady state shape (i.e., fully deployed state). The struts, the anchors, or both may progressively open from the retracted state to the deployed state over a period of time (e.g., 6 hours or more, 12 hours or more, 24 hours or more, 1 day or more, 3 days or more, or even 1 week or more) so that a passage, airway, or both is progressively sealed as the struts fully open. The struts, the anchors, or both may rapidly open into contact with the structure such as a passageway (e.g., 5 minutes or less, 3 minutes or less, 1 minute or less, or even 30 seconds or less).

The retracted state may have the valve located within a capsule, a cartridge, a catheter, a bronchoscope, or a combination thereof. The retracted state may have the struts, anchors, or both extending substantially parallel to the longitudinal axis. The retracted state may have the struts, anchors, or both pointing away from the distal end, towards, the proximal end, or both. The retracted state may have the struts, anchors, or both pointing in a direction so that during placement the struts do not inadvertently connect to any passages, walls, tissue, or a combination thereof. The retracted state may have the valve compacted so that the valve may travel through one or more passages, one or more air ways, a catheter, a bronchoscope, or a combination thereof. The retracted state may allow the valve to travel through tortuous passages, airways, or both without connecting to the walls, tissue, or both. The retracted state may allow the valve to be placed in a second division, a third division, or even a fourth division of the airway tree. The retracted state may be ended once the valve is ejected from, released from, removed from, or a combination thereof a capsule, a cartridge, a catheter, a bronchoscope, or a combination thereof.

The valve may be loaded into a cartridge so that the struts are maintained is a folded configuration, a parallel relationship to the longitudinal axis, or both. The valve may be ejected from the cartridge so that any pressure on the struts by the cartridge is released. The cartridge may be used to load the valve into a deployment device such as a bronchoscope. The endoscope, bronchoscope, or both may be pulled backwards as the cartridge, valve, or both are released so that the valve is placed within a passage, an airway, or both. The endoscope, bronchoscope, or both may be pulled back so that the valve is maintained in a desired location, a predetermined location, at a collapsed location, or a combination thereof. Once the valve is deployed the struts may function to begin elastically deforming. The struts may be configured so that the struts sea; a passage, an airway, or both as the struts elastically deform. The struts may be connected to the anchor and may form a connection with a passage, tissue, airway, a wall, or a combination thereof so that axial movement of the strut is substantially prevented.

Figure 1A:
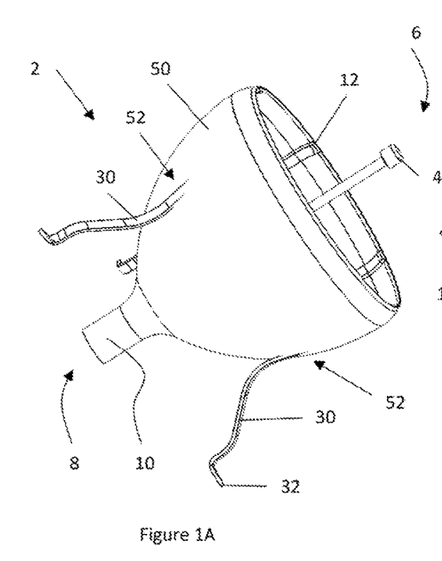
FIG. 1A illustrates a perspective view of a valve.

FIG. 1A illustrates a perspective view of a valve 2. The valve 2 includes a frame 10 with a plurality of struts 12 that extend radially outward as the struts 12 extend from the distal end 8 towards the proximal end 6. The struts 12 are covered by a membrane 50. Some of the struts 12 are connected to an anchor 30 that extends through an exit location 52 in the membrane 50 outward away from the valve 2 so that the anchors 30 can attach the valve to a surrounding structure (not shown) such as an airway via the one or more anchor tips 32 on each anchor 30. A rod 4 extends substantially along a center of the valve 2, the rod 4 assisting in deploying the valve 2.

Figure 1B:
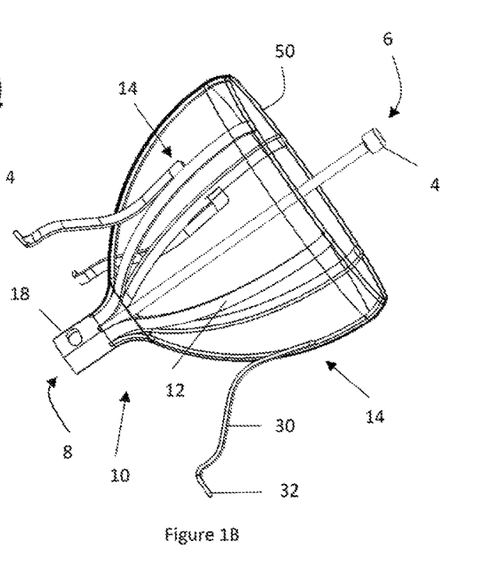
FIG. 1B illustrates the valve of FIG. 1A with the membrane removed.

FIG. 1B illustrates the valve of FIG. 1A with the membrane 50 shown as transparent so that the frame 10 is visible. The frame 10 is joined at the distal end 8 and expands radially outward towards the proximal end 6. A rod 4 extends along the longitudinal axis of the valve 2. The frame 10 includes a plurality of struts 12 that are directly connected to anchors 30 by anchor connections 14. The anchors 12 extend from an inside of the membrane 50 to an outside of the membrane 50 so that the anchor tips 32 of the anchors 12 can contact a feature of interest.

Figure 2:
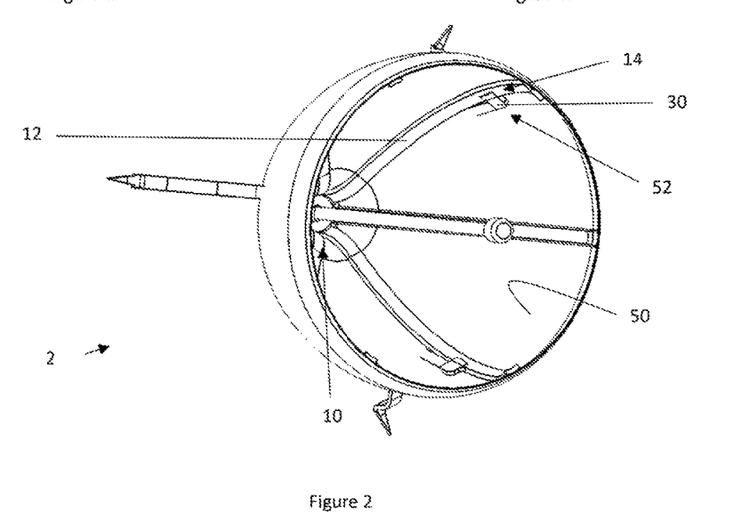
FIG. 2 illustrates a front perspective view of a valve.

FIG. 2 illustrated a perspective view of the valve 2 from the proximal end so that an inside of the frame 10 and membrane 50 are visible. Struts 12 are shown connected to the rod 4 by a base member 18 and extending towards the proximal end and expanding radially outward. Anchors 30 are connected to the struts 12 via anchor connections 14. The anchors 30 extend through the membrane 50 towards the distal end as the anchors 30 extend radially outward.

Figure 3:
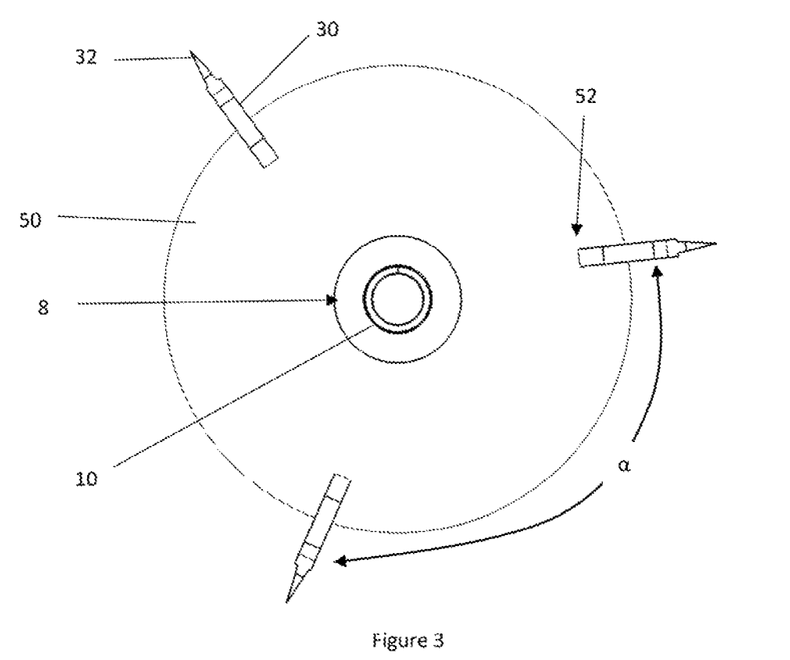
FIG. 3 illustrates a rear view of a valve.

FIG. 3 is a view of the valve 2 from the distal end 8. The frame 10 as shown forms a connection point substantially in the center of the valve 2 where the struts (not shown) extend therefrom. The anchors 30 extend through the membrane 50 at an exit location 52 extend radially outward. The anchors 30 are separated by a distance (a) and each anchor 30 includes an anchor tip 32.

Figure 4:
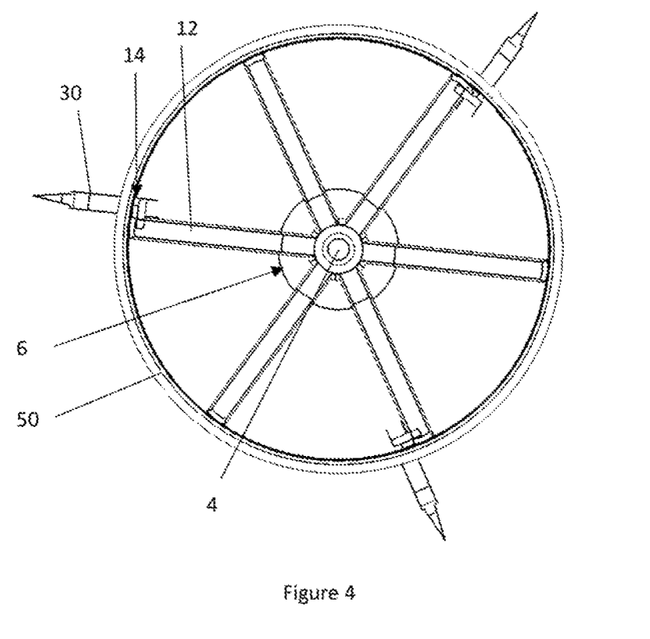
FIG. 4 illustrates a front view of a valve.

FIG. 4 illustrates a view of the valve 2 from the proximal end 6. The rod 4 extend from a center of the valve 2. The struts 12 extend radially outward to expand the membrane 50. Anchors 30 are connected to the struts at the anchor connection 14 and extend radially outward from the struts 12 and beyond the struts 12.

Figure 5:
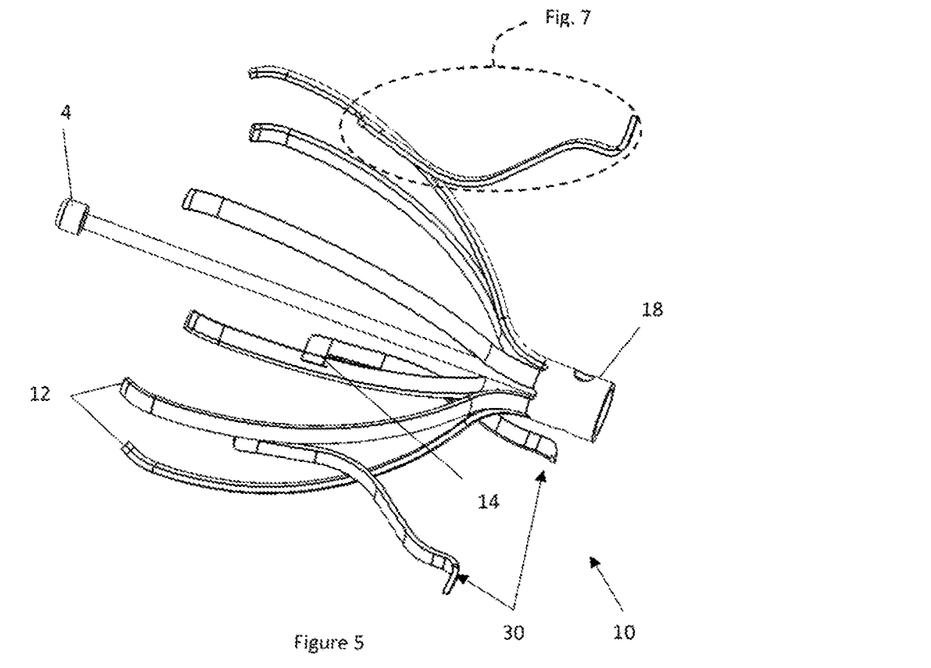
FIG. 5 illustrates a perspective view of a frame.

FIG. 5 illustrates a perspective view of the frame 10. The frame 10 includes a rod 4 that is surrounded by a plurality of struts 12, which are connected to the rod 4 by a base member 18. Each of the struts 12 have a tip region that extends inward towards the rod 4. Each of the struts 12 is connected to an anchor 30 at an anchor connection 14. The anchors 30 then extend away from the struts 12.

Figure 6:
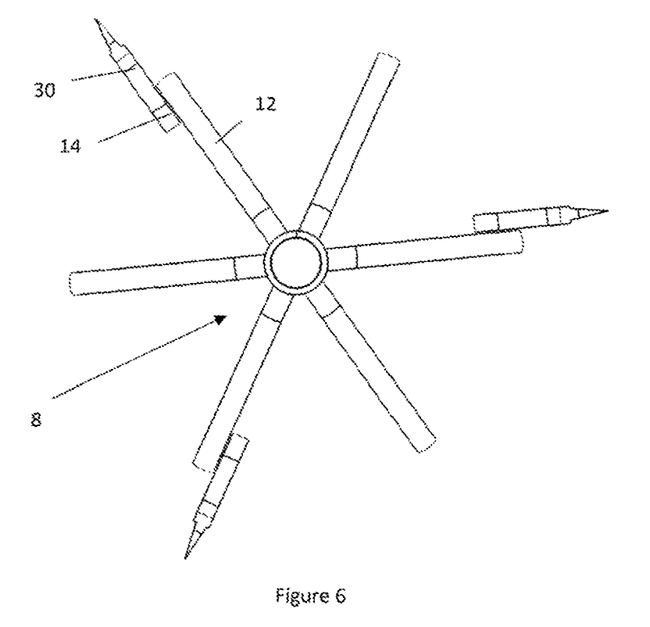
FIG. 6 illustrates a rear view of a frame.

FIG. 6 illustrates a distal end 8 view of the frame 10 with the struts 12 and the anchors 30 extending radially outward. The anchors 30 extend radially beyond the struts 12. The struts 12 and anchors 30 are joined at an anchor connection 14 and the struts 12 and anchors 30 are located substantially side by side.

Figure 7:
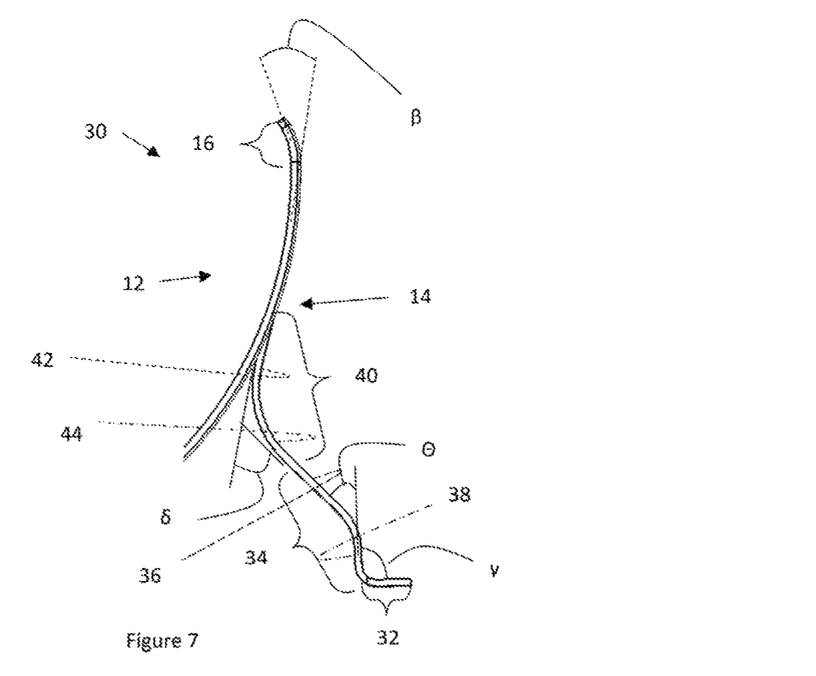
FIG. 7 illustrates a close-up view of one strut and one anchor of FIG. 6.

FIG. 7 illustrates a close-up plan view of one strut 12 and one anchor 30. The strut 12 is generally arcuate along its length and includes an angled tip 16 that forms an angle ($\beta$) with the strut 12 so that the angled tip 16 angles inward. The anchor 30 has an anchor connector 14 with the strut 12 and then has a serpentine shape as the anchor extend away from the strut 12. The anchor 30 has a first arcuate region 40 that has a connection segment 42 extends generally downward and away from the strut 12 and a transition segment 44 that extends outward from the connection segment 42 at an angle ($\delta$). The first arcuate region 40 transitions into a second arcuate region 34 at a transition segment 44. The transition segment 44 of the first arcuate region 40 connects to a radial segment 36 of the second arcuate segment 34. The radial segment 36 is connected to a longitudinal segment 38 (which may be used as an anchor pad) that extends generally outward and downward from the strut 12 and the radial segment 36 at an angle ($\Theta$). The second arcuate region 34 is located between and connects the first arcuate region 40 and the anchor tip 32. The anchor tip 32 and the first arcuate region 40 form an angle ($\gamma$) so that anchor tip can engage and retain the valve in place.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

2 Valve
4 Rod
6 Proximal end
8 Distal end
10 Frame
12 struts
14 Anchor connection
16 Angled tip
30 Anchor
32 Anchor tip
34 Second arcuate region
36 Radial segment
38 Longitudinal segment
40 First arcuate region
42 Connection segment
44 Transition segment
50 membrane
52 Exit location

I claim:

1. A valve comprising:
   a. membrane and
   b. a frame in communication with the membrane so that the frame expands the membrane, the frame including:
      i. a rod,
      ii. a plurality of struts connected to the rod at a distal end and extending generally radially outward as the struts extend away from the distal end and towards a proximal end;
      iii. a plurality of anchors that are in direct communication with the struts between the distal end and the proximal end, each of the plurality of anchors extending through an exit location in the membrane; and
      iv. an anchor connector extending between and connecting the plurality of anchors to the plurality of struts; and
   wherein each of the anchor connectors extend laterally from one of the plurality of struts.

2. The valve of claim 1, wherein some of the plurality of struts are free of the plurality of anchors.

3. The valve of claim 1, wherein each of the plurality of anchors extend towards the distal end of the valve as each of the plurality of anchors extend away from the struts.

4. The valve of claim 1, wherein the struts have a generally arcuate shape and extend outward from the rod.

5. The valve of claim 1, wherein one or more of the plurality of struts include an angled tip that is angled towards from the rod.

6. A valve comprising:
   a. membrane and
   b. a frame in communication with the membrane so that the frame expands the membrane, the frame including:
      i. a rod,
      ii. a plurality of struts connected to the rod at a distal end and extending generally radially outward as the struts extend away from the distal end and towards a proximal end;
      iii. a plurality of anchors that are in direct communication with the struts between the distal end and the proximal end, each of the plurality of anchors extending through an exit location in the membrane; and
      iv. an anchor connector extending between and connecting the plurality of anchors to the plurality of struts; and
   wherein the plurality of anchors each extend from a side of the plurality of struts that each of the plurality of anchors are connected.

7. A valve comprising:
   a. membrane and
   b. a frame in communication with the membrane so that the frame expands the membrane, the frame including:
      i. a rod,
      ii. a plurality of struts connected to the rod at a distal end and extending generally radially outward as the struts extend away from the distal end and towards a proximal end;
      iii. a plurality of anchors that are in direct communication with the struts between the distal end and the proximal end, each of the plurality of anchors extending through an exit location in the membrane; and
      iv. an anchor connector extending between and connecting the plurality of anchors to the plurality of struts; and
   wherein each of the anchors include an anchor tip that extends outward away from the rod.

8. The valve of claim 1, wherein each of the plurality of anchors include a first arcuate region that curves each of the plurality of anchors away from each of the plurality of struts.

9. The valve of claim 8, wherein the first actuate region curves at an angle of about 45 degrees or more and about 150 degrees or less.

10. The valve of claim 9, wherein the angle of the first arcuate region curves at an angle between about 60 degrees and about 105 degrees.

11. The valve of claim 8, wherein each of the plurality of anchors include a second arcuate region.

12. The valve of claim 11, wherein the second arcuate region curves each of the plurality anchors towards the distal end, and the second arcuate region curves at an angle of about 10 degrees or more and about 90 degrees or less.

13. The valve of claim 1, wherein each of the plurality of anchors are located about 45 degrees or more apart and about 180 degrees or less.

14. The valve of claim 12, wherein the second arcuate region curves at an angle of about 20 degrees and about 45 degrees.

15. The valve of claim 13, wherein each of the plurality of anchors are located about 90 degrees or more apart and about 135 degrees or less.

16. The valve of claim 6, wherein each of the plurality of anchors extend towards the distal end of the valve as each of the plurality of anchors extend away from the struts, and wherein the struts have a generally arcuate shape and extend outward from the rod.

17. The valve of claim 6, wherein each of the plurality of anchors include a first arcuate region that curves each of the plurality of anchors away from each of the plurality of struts.

18. The valve of claim 17, wherein each of the plurality of anchors include a second arcuate region, and the second arcuate region curves each of the plurality anchors towards the distal end, and the second arcuate region curves at an angle of about 10 degrees or more and about 90 degrees or less.

19. The valve of claim 7, wherein each of the plurality of anchors extend towards the distal end of the valve as each of the plurality of anchors extend away from the struts, and wherein the struts have a generally arcuate shape and extend outward from the rod.

20. The valve of claim 7, wherein each of the plurality of anchors include a first arcuate region that curves each of the plurality of anchors away from each of the plurality of struts and each of the plurality of anchors include a second arcuate region, and the second arcuate region curves each of the plurality anchors towards the distal end, and the second arcuate region curves at an angle of about 10 degrees or more and about 90 degrees or less.

\* \* \* \* \*